(12) United States Patent
Swaminathan et al.

(10) Patent No.: US 10,083,274 B2
(45) Date of Patent: Sep. 25, 2018

(54) NON-HYPERGEOMETRIC OVERLAP PROBABILITY

(71) Applicant: Regeneron Pharmaceuticals, Inc., Tarrytown, NY (US)

(72) Inventors: Karthikeyan Swaminathan, San Jose, CA (US); Wen Fury, New York, NY (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 0 days.

(21) Appl. No.: 15/648,164

(22) Filed: Jul. 12, 2017

(65) Prior Publication Data

US 2017/0308642 A1 Oct. 26, 2017

Related U.S. Application Data

(60) Continuation of application No. 13/595,355, filed on Aug. 27, 2012, now abandoned, which is a division of application No. 12/535,179, filed on Aug. 4, 2009, now Pat. No. 8,255,167.

(60) Provisional application No. 61/088,884, filed on Aug. 14, 2008.

(51) Int. Cl.
*G06F 19/00* (2018.01)
*G06F 19/20* (2011.01)
*G06F 19/24* (2011.01)

(52) U.S. Cl.
CPC .............. *G06F 19/20* (2013.01); *G06F 19/24* (2013.01)

(58) Field of Classification Search
CPC ............ C12Q 2600/158; C12Q 1/6886; C12Q 2600/112; C12Q 2600/142; G06F 19/24; G06F 19/18; G06F 19/20; G06F 19/34; G06F 19/345; G06F 19/12; G06F 19/28; G01N 2800/52; G01N 2800/56;
(Continued)

(56) References Cited

U.S. PATENT DOCUMENTS 5,622,823 A 4/1997 Perlin
6,203,987 B1 3/2001 Friend et al.
6,502,039 B1 12/2002 Theilhaber et al.
(Continued)

FOREIGN PATENT DOCUMENTS

EP 2324351 5/2011
WO WO-2010/019420 2/2010

OTHER PUBLICATIONS

U.S. Appl. No. 61/088,884, filed Aug. 14, 2008, Karthikeyan Swaminathan.
(Continued)

*Primary Examiner* — Mary K Zeman
(74) *Attorney, Agent, or Firm* — Ballard Spahr LLP

(57) ABSTRACT

Methods, software, and systems are provided for determining the probability of an overlap set of entities having an overlap size, where the overlap set is independently selected from two sets of non-identical entities. Applications of the invention to microarrays are provided. Probability distributions are provided for determining the probability that the size of an overlap gene set from two different microarrays occurs by chance. Microarray analysis for determining the size of a statistically significant overlap gene set given two different microarrays is described. Overlap set size probability determinations that account for the total number of genes in two different microarrays and not just the common genes are described.

22 Claims, 7 Drawing Sheets

(58) Field of Classification Search
CPC ........... G01N 33/57484; G01N 33/574; G01N 33/57423; G01N 33/57434; G01N 2800/60
See application file for complete search history.

(56) References Cited

U.S. PATENT DOCUMENTS

| | | | |
|---|---|---|---|
| 6,691,042 | B2 | 2/2004 | Weng et al. |
| 6,746,844 | B2 | 6/2004 | Oliner et al. |
| 6,915,282 | B1 | 7/2005 | Conway et al. |
| 6,942,968 | B1 | 9/2005 | Dickinson et al. |
| 7,020,561 | B1 | 3/2006 | McLoughlin et al. |
| 7,117,188 | B2 | 10/2006 | Guyon et al. |
| 7,197,400 | B2 | 3/2007 | Liu et al. |
| 7,243,112 | B2 | 7/2007 | Qu et al. |
| 7,353,116 | B2 | 4/2008 | Webb et al. |
| 7,363,165 | B2 | 4/2008 | Tusher et al. |
| 8,007,995 | B2 | 8/2011 | Finn et al. |
| 8,255,167 | B2 | 8/2012 | Swaminathan et al. |
| 2004/0254350 | A1 | 12/2004 | Ho et al. |
| 2006/0074290 | A1 | 4/2006 | Chen et al. |
| 2007/0162411 | A1 | 7/2007 | Kupershmidt et al. |
| 2007/0178473 | A1 | 8/2007 | Chen et al. |
| 2010/0042330 | A1 | 2/2010 | Swaminathan et al. |
| 2012/0323497 | A1 | 12/2012 | Swaminathan et al. |

OTHER PUBLICATIONS

U.S. Appl. No. 12/535,179 (U.S. Pat. No. 8,255,167), filed Aug. 4, 2009 (Aug. 28, 2012), Karthikeyan Swaminathan.
U.S. Appl. No. 13/595,355, filed Aug. 27, 2012, Karthikeyan Swaminathan.
EP, 09807080.8 (EP 2324351), Aug. 5, 2009 (May 25, 2011), (Regeneron Pharmaceuticals, Inc.).
PCT, PCT/US2009/052785 (WO 2010/019420), Aug. 5, 2009 (Feb. 18, 2010), (Regeneron Pharmaceuticals, Inc.).
EP 09807080 Supplemental Search Report and Search Opinion completed Jul. 14, 2011.
International Search Report and Written Opinion dated Sep. 17, 2009 by the International Searching Authority for International Application No. PCT/US2009/052785, which was filed on Aug. 5, 2009 and published as WO 2010/019420 on Feb. 18, 2010 (Applicant—Regeneron Pharmaceuticals, Inc.) (6 pages).
International Preliminary Report on Patentability was dated Feb. 15, 2011 by the International Searching Authority for International Application No. PCT/US2009/052785, which was filed on Aug. 5, 2009 and published as WO 2010/019420 on Feb. 18, 2010 (Applicant—Regeneron Pharmaceuticals, Inc.) (5 pages).
Supplementary European Search Report was dated Jul. 25, 2011 by the International Searching Authority for International Application No. 098070808, which was filed on Aug. 5, 2009 and published as EP 2324351 on May 25, 2011 (Applicant—Regeneron Pharmaceuticals, Inc.) (6 pages).
Bossotti, R. et al. (2007) Cross platform microarray analysis for robust identification of differentially expressed genes, BMC Bioinformatics 8 (Suppl. 1):S5.
Choi, J. K.et al. (2003) Combining multiple microarray studies and modeling interstudy variation, Bioinformatics 19(Suppl. 1):i84-i90.
Cui, X. et al. (2003) .Statistical test for differential expression in cDNA microarray experiments, Genome Biology 4:210.
Culhane A. et al. (2003) Cross Platform comparison and visualization of gene expression data using co-inertia analysis, BMC Bioinformatics 4:59.
Curtis, r. et al. (2005) Pathways to the analysis of microarray data, Trends Biotech. 23(8):429-435.
Dudoit, S. et al. (2000) Statistical methods for identifying differentially expressed genes in replicated cDNA microarray experiments, Technical Report #578, Dept. Biochem, Stanford Univ., Stanford CA.
Fury W. et al. (2006) Overlapping probabilities of top ranking genes lists, hypergeometric distr . . . Proc., of the 28th iEEE, EMB Ann. International conference, NYC Aug. 30-Sep. 3 06:5531-5534.
Glinsky, G. et al. (2005) Microarray analysis identifies a death-from-cancer signature predicting therapy failure in patients with multiple types of cancer, J Clin. Invest. Jun. 2005; 115(6):1503-21.
Hong, F. et al. (2008) A comparison of meta-analysis methods for detecting differentially expressed genes in microarray experiments, Bioinformatics 24(3):374-382.
Jiang, H. et al. (2004) Joint analysis of two microarray gene-expression data sets to select lung adenocarcinoma marker genes, BMC Bioinformatics 5:81.
Kuo, W. et al. (2002) Analysis of matched mRNA measurements from two different microarray technologies, Bioinformatics 18(3):405-412.
Lee, H. et al. (2004) Coexpression analysis of human genes across many microarray data sets, Genome Res. 14:1085-1094.
Leung, Y. et al., (2003) Fundamentals of cDNA microarray data analysis, trends Genet. 19(11):649-659.
Pan W. (2002) A comparative review of statistical methods for discovering differentially expressed genes in replicated microarray experiments, bioinformatics 18(4)546-554.
Pan F. et al (2006) Integrative Array Analyzer: a software package for analysis of cross-platform and cross species microarray data, Bioinformatics 22(13)1665-1667.
Park T. et al.(2006) combining multiple microarrays in the presence of controlling variables, Bioinformatics 22(14):1682-1689.
Parmigiani, G. et al. (2004) A Cross-study comparison of gene expression studies for the molecular classification of lung cancer, Clin. Cancer Res. 10:2922-2927.
Rhodes, D. et al. (2002) Meta-analysis of microarrays: interstudy validation of gene expression profiles reveals pathway dysregulation in prostate cancer, Cancer Res. 62:4427-4433.
Rhodes, D. et al. (2004) Large-scale meta-analysis of cancer microarray data identifies common transcriptional profiles of neoplastic transformation and progression, PNAS USA 101(25):9309-9314.
Stafford, P. et al. (2007) Three methods for optimization of cross-laboratory and cross-platform microarray expression data, Nucleic Acids Res. 35(10):e72, 1-16.
Warnat, P. et al. (2005) Cross-platform analysis of cancer microarray data improves gene expression based classification of phenotypes, BMC Bioinformatics 6:265.
Subrmanian A., et al, "Gene set enrichment analysis: a knowledge-based approach for interpreting genome-wide expression profiles", PNAS, (2005); 102(43): 15545-15550.
Fall N, et al. (2007) "Gene expression profiling of peripheral blood from patients with untreated new-onset systemic juvenile idiopathic arthritis reveals molecular heterogeneity that may predict macrophage activation syndrome" Arthritis Rheum. 56(11):3793-804.
Liu, Z. et al. (2006) "Identification of gene expression signatures in autoimmune disease without the influence of familial resemblance" Hum Mol. Genet. 15(3):501-9.
Communication Pursuant to Article 94(3) EPC dated Jan. 9, 2018 by the European Patent Office for Patent Application No. 09807080.8, which was filed on Aug. 5, 2009 and published as EP 2324351 on May 25, 2011 (Inventor—Swaminathan et al.; Applicant—Regeneron Pharmaceuticals, Inc.; (9 pages).

NON-HYPERGEOMETRIC OVERLAP PROBABILITY

This is a continuation of U.S. Non-provisional application Ser. No. 13/595,355 filed Aug. 27, 2012, which is a divisional of U.S. Non-provisional application Ser. No. 12/535,179 filed Aug. 4, 2009, now issued as U.S. Pat. No. 8,255,187, which claims benefit of U.S. Provisional Application No. 61/088,884 filed Aug. 14, 2008, each of which is herein incorporated by reference in their entirety.

FIELD OF INVENTION

The invention relates to combinatorics, probability theory, and methods, computer software products, and systems for determining the probability that the number of overlap entities between two sets of different entities is by chance. The invention also relates to methods, products, and systems for determining the probability that the number of overlapping genes generated from two different types of microarrays is by chance.

BACKGROUND

Methods for determining the probability of the size of overlap of two sets of data picked independently and randomly from the same population are known in the art. A method of choice for determining the statistical significance of such an overlap is to employ the hypergeometric distribution. Methods for determining the probability of overlap of two sets of data picked independently and randomly from two different but overlapping populations are also known. However, these methods either oversimplify the problem in order to employ the hypergeometric distribution, in which case the accuracy is compromised (except in the limiting case where the two populations have a complete overlap); or the methods employ a permutation method to determine the probability, in which case the solution is also approximate and very time consuming.

For the specific case of microarrays, the use of the hypergeometric distribution for determining the overlapping probability of two gene signatures derived from two experiments using the same chip type is known. Further, when the two experiments being compared are from different chip types, the current practice is to so reduce the problem by considering only those genes that are common between both chips so that the hypergeometric distribution can be utilized. See, for example, GeneSpring™ (Agilent Technologies, Inc.), and Resolver™ (Rosetta Inpharmatics, LLC). Alternatively, a random permutation technique is available in Oncomine™ (Compendia Bioscience Inc.).

Thus, there is a need for a simple and accurate method that can determine the probability of overlap when the underlying populations are different and overlapping. In particular, there is a need for an easy to use and accurate method of determining the probability of overlap between two sets of genes selected from two different but overlapping microarray chips.

SUMMARY

Methods, computer products, software, and systems for analyzing sets of entities derived from two populations are provided. In various aspects, applications for analyzing sets of entitles derived from two nonidentical populations are provided. The analysis results in a comparative metric comprising a probability score that denotes the probability that an overlap set, formed by independent draws each from different and possibly intersecting sets of entities, is obtained by chance, phrased herein as the "overlap probability." Methods, computer products, software, and systems for providing metrics related to or derived from the overlap probability are also provided.

In one aspect, a probability score is determined by a method that comprises the steps of: providing a first subset of entities from a first entity set, providing a second subset of entitles from a second entity set, wherein the first entity set and the second entity set are not necessarily identical, and wherein the first subset of entities and the second subset of entities overlap at least in part to form an overlap set; and determining the probability that this overlap set is drawn by chance, wherein determining the probability that the overlap set is drawn by chance includes taking into account that the probability depends at least in part of on a function of the total number of ways of selecting the first subset of entities set from all entities of the first entity set and also depends at least in part on a function of the total number of ways of selecting the second subset of entities from all entitles of the second entity set. In one aspect, the first entity set and the second entity set are not identical.

In a more particular aspect, the probability that the number of overlap set is by chance comprises determining the number of ways of selecting the overlap set from ail entities common to both the first entity set and the second entity set, divided by: (a) the number of ways of selecting the first subset, of entities from the first entity set, multiplied by (b) the number of ways of selecting the second subset of entitles from the second entity set.

In a more particular aspect, the number of ways of selecting the overlap set from all entities common to both the first entity set and the second entity set is multiplied by a sum, over the minimum of either (a') the number of entities of the first subset of entities that are not common with the second subset of entitles, or (b') the number of entities common between the two entity sets excluding the number of entities common between the two subsets, of: (a") the number of ways of choosing entities in that part of the first subset of entitles that are included in the second entity set but not in the overlap set, from the number of common entities between the two entity sets excluding the overlap set, multiplied by (b") the number of ways of choosing that part of the first subset of entities that are not included in the second entity set, from the number of entities in the first entity set excluding the entities common with the second entity set multiplied by (c") the number of ways of choosing the number of entities in that part of the second subset of entities that are not in the overlap set, from the number of entities in the second entity set excluding those entities in the first subset of entities.

In a more particular aspect, the overlap probability is determined using the formula $$p(m) = \frac{C(M, m) \sum_{i=0}^{min(x-m, M-m)} [(C(M-m, i))(C(X-M, x-i-m))(C(Y-m-i, y-m))]}{(C(X, x))(C(Y, y))}$$

wherein:

X is the number of entities in the first entity set:
Y is the number of entities in the second entity set;

M represents the size of the set of entities common to both the first entity set and the second entity set, or in other words, represents the number of entities in common between the first and the second entity set;

x is the number of entities of the first subset of entities chosen from the first entity set;

y is the number of entities of the second subset of entities chosen from the second entity set;

m is the number of entities in an overlap set, wherein the overlap set is formed by entities common to both the first subset of entities and the second subset of entities; and, p(m) is the probability of selecting any overlap set of size m by chance, wherein the overlap set is a set formed by entities common to the first subset of entities and the second subset of entities.

In various aspects, computer-implemented methods, computer products, software, and systems for determining the comparison metric are provided, as well as for providing other metrics derived from or related to the comparison metric. The aspects include a computer product comprising computer-readable and computer-implementable instructions comprising steps for determining the overlap probability in accordance with the above-described formula. Other metrics derived from or related to the comparison metric include, but are not limited to, the size of the minimum overlap set at a given statistical significance (e.g., p-value of a given statistical significance), and the cumulative overlap probability.

In various aspects, computer-implemented methods, computer software products, and systems are provided for determining the comparison metric and other metrics derived from or related to the metric are provided for application to microarray analysis, where the arrays are not necessarily identical. In one aspect, the arrays are not identical. The microarrays include, but are not limited to, nucleotide arrays and protein arrays and single nucleotide polymorphism (SNP) arrays. In various aspects, the microarrays can comprise, for purposes of illustration but not limitation, polynucleotides representing genes, biomarkers and single nucleotide polymorphisms (SNP) polypeptides representing proteins, protein domains and antibodies.

BRIEF DESCRIPTION OF THE FIGURES

The following illustrations are provided to assist in explaining embodiments of the subject matter described herein, and are not intended to limit the scope of the invention.

DETAILED DESCRIPTION

Figure 1:
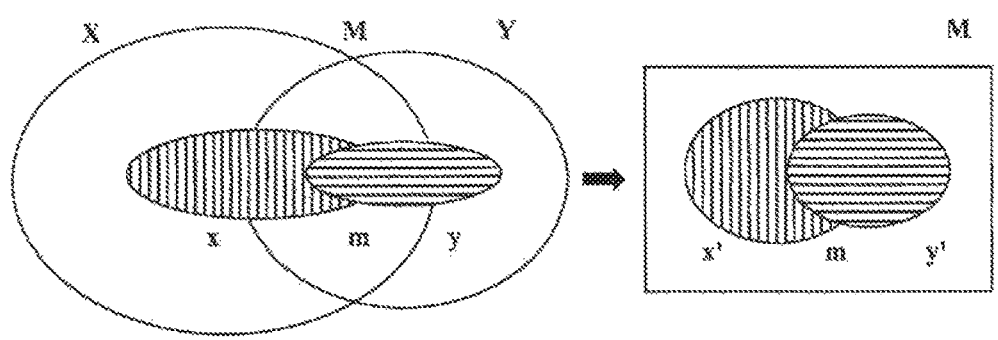
FIG. 1 illustrates parameters considered in calculating an overlap probability (left) and parameters considered in calculating hypergeometric probability (right).

Before the present methods are described, it is to be understood that this invention is not limited to specific methods and experimental conditions described; as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an," and "the" include plural references unless the context clearly dictates otherwise. Thus for example, a reference to "a method" includes one or more methods, and/or steps of the type described herein and/or which will become apparent, to those persons skilled in the art upon reading this disclosure.

Unless defined otherwise, or otherwise specified, all technical and scientific terms used herein have the same meaning as commonly understood by one of ordinary skill in the art to which this invention pertains.

Although any methods and materials similar or equivalent to those described herein can be used in the practice or testing of the present invention, particular methods and materials are now described. Each of the recited patents, applications, and publications are incorporated herein by reference in their entirety; cited portions are of the patents and applications incorporated herein by reference are also independently incorporated herein by reference.

The invention is based at least in part on the realization that an accurate determination of the probability of obtaining an overlap set of a given size from two subsets of entitles independently drawn from two entity sets, under many circumstances, is not always accurately given by methods employing the hypergeometric probability. Where the overlap set results from the overlap of a first subset of entitles selected from a first entity set, and a second subset of entities selected from a second entity set, and the first entity set is not identical to the second entity set, the use of hypergeometric probability results in an inaccurate measure of the actual probability of drawing an overlap set of a given size. Instead, an accurate measure of the actual probability, referred to herein as the "overlap probability," is a function of an expression that includes considering the product of all number ways of drawing the first subset of entities from the first entity set and all number of ways of drawing the second subset of entities from the second entity set.

A formula that, incorporates this consideration and provides the overlap probability is described herein, as well as computer-implemented methods, a computer software product, and computer systems for analyzing microarray data and for providing overlap probability.

Although the majority of the description employs an application concerning gene microarrays, the overlap probability method is not limited to application to gene microarrays, but can generally be applied to any two sets of entities. Where the two sets of entities are identical (i.e., they are made up of the same entities), the overlap probability will equal the hypergeometric probability. Where the two sets of entities are non-identical (i.e., where some entities exist in one set hut not in the other), the hypergeometric probability and the overlap probability will diverge. In such a case, the overlap probability will yield the accurate estimation of the actual probability.

Two microarray experiments that result in identifying an overlapping set of genes (i.e., an overlap set) can provide potentially biologically significant information about the genes in the overlap set, and/or about the samples used in the microarray experiments and/or insights into the underlying relationship between the two biological studies. It is therefore desirable to determine the likelihood that an overlap set would occur by chance. If an overlap were very unlikely to occur by chance, then biological significance of the overlap is, generally, more likely, if a comparison of an observed overlap and a calculated overlap is statistically significant a stronger inference regarding biological significance might be made.

The methods, software, and systems described herein can be used to determine the overlap probability for any array experiment, and, in particular, for two array experiments wherein the platforms are not identical. It is intended that the term "genes," the phrase "gene sets," the phrase "gene subsets," and the like, when referring to arrays, includes reference to segments of genes, (e.g., polynucleotides containing a sufficient amount of nucleotide sequence to identify the polynucleotide as belonging to particular whole gene). For example, a polynucleotide of an array can be representative of a gene.

The term "microarray," or "array," as used herein is intended to include articles of manufacture falling within the descriptions of arrays (and methods of using them) provided in the following U.S. Pat. No. 7,115,384 (see, e.g., col. 1, line 57-col. 7, line 20; also, col. 12, line 5-col. 22, line 4); U.S. Pat. No. 7,208,439 (see, e.g., col. 4, lines 5-40); U.S. Pat. No. 7,130,458 (see, e.g., col. 5, line 33-col. 7, line 25); U.S. Pat. No. 7,243,112 (see, e.g., col. 4, lines 44-87); U.S. Pat. No. 8,691,042 (see, e.g., cols. 1-3); (see, e.g., col. 23, line 32-col. 41, line 19); U.S. Pat. No. 8,502,039 (see, e.g., col. 3, line 49-col. 4, line 59); U.S. Pat. No. 7,361,908 (see, e.g., cols. 1-7, and col. 4, line 60-col. 6, line 13; col. 10, line 11-col. 11, line 58); U.S. Pat. No. 7,353,116 (polymer arrays or chemical arrays; see. e.g. cols. 1-2: col. 3, line 35-col. 4, line 44; U.S. Pat. No. 5,985,352 (e.g., arrays for determining drug response; see, e.g., col. 43, line 36-col. 50, line 27); U.S. Pat. No. 7,291,471 (e.g., cleavable arrays; see. e.g., col. 11, line 41-col. 14, line 65); U.S. Pat. No. 7,221,785 (see, e.g., col. 10, line 1-col. 12, line 46); U.S. Pat. No. 7,374,927 (e.g., including compromised samples, see, e.g., col. 12, line 38-col. 18, line 9); U.S. Pat. No. 7,381,488 (e.g., for SNP analysis, see, e.g.: col. 3, line 7-col. 5, line 42; also col. 12, line 36-col. 17, line 22); U.S. Pat. No. 7,341,835 (e.g., for splice variants, see, e.g., col. 1, line 24-col. 2, fine 32; also col. 10, line 40-col. 14, line 22); U.S. Pat. No. 7,323,308 (e.g., for *E. coli*); U.S. Pat. No. 7,314,750 (e.g., for rats); U.S. Pat. No. 7,312,035 (e.g., for yeast); U.S. Pat. No. 729,777 (e.g., for genotyping); U.S. Pat. No. 7,252,948 (e.g., for mycobacteria); U.S. Pat. No. 7,250,289 (e.g., mice); U.S. Pat. No. 7,144,899 (e.g., sequencing array); U.S. Pat. No. 7,097,976 (e.g., arrays for defecting allelic imbalance); U.S. Pat. No. 6,927,032 (e.g., expression-monitoring array); U.S. Pat. No. 6,919,211 (e.g., polypeptide array); U.S. Pat. No. 6,884,101 (e.g., ligand/polymer array); U.S. Pat. No. 6,746, 844 (e.g., signal transduction); U.S. Pat. Nos. 6,586,186 and 6,582,908 (e.g., polymorphism array); and TaqMan™ Gene Signature Arrays (Applied Biosystems).

Any suitable array known in the art can be used in connection with the methods, software, and systems described herein. Non-limiting examples of arrays known in the art are described herein by incorporation by reference. Alternatively, custom arrays may be printed using any array-printing method known in the art.

As applied to microarray analysis, overlap probability methods described herein include methods that calculate significance (i.e., p-values) of an overlap set of genes of a given size, between two microarray experiments. The overlap probability method determines the probability that an observed overlap between two microarray experiments would occur by chance in various embodiments this can be achieved by calculating an overlap probability for two microarray experiments, then comparing overlap observed in the experiment with calculated overlap probability for the two microarrays. If the overlap probability method calculates that an observed overlap is unlikely to be observed by chance, then the observed overlap may have biological significance. Determining the statistical significance of the comparison can provide support for inferences about a likely biological significance associated with the identity of the genes of the overlap set.

Biologically significant insights from a microarray comparison analysis frequently rely on the accuracy of the underlying statistical model used to analyze the array. Microarray analysis frequently includes comparing gene sets identified under a first set of conditions with gene sets identified under a second set of conditions, using a different microarray platform, and an overlap gene set identified, identifying members of the overlap set can lead to biological insights resulting from their presence in the overlap set, depending upon the different conditions. In certain circumstances, identifying members of the overlap set can be dispositive of a biological question, for example, the overlap set might define a prognostic indicator, a set of biomarkers for a disease or disorder, susceptibility for a disease or disorder, or a significant expression signature. In order to generate a reliable overlap set, reliable information about the statistical significance of the overlap set is often needed.

Depending upon the microarrays used and conditions selected, multiple array comparisons can sometimes give rise to high degrees of noise and low reproducibility. In clinical and other practical applications, misidentification of signature profiles can potentially be life-threatening in the case of false negatives, and burdensome for patients in the case of false positives, both of which are important concerns given overlap variability using presently available models that reveal varying overlap between platforms.

As described above, the overlap probability method is a general method that can be used to calculate the statistical significance of the overlap size between two lists of entities that are derived independently from two overlapping populations. One application of the method is to compare gene lists across different microarray platforms, and even platforms of different species. The method is based at least in part on the realization that an accurate statistical significance can be achieved by including all genes, shared or not shared, in comparing two microarray experiments, including experiments where two microarrays do not assay for all of the same genes. Thus, the probability of observing an overlap set of a defined size depends not simply on the number of shared genes between the microarray chips (as for the hypergeometric probability), but on the total number of genes of each microarray chip.

Identification of overlapping gene sets in microarray experiments is presently mainly achieved using methods that rely on the hypergeometric distribution. The hypergeometric distribution method assumes that, given two sets of genes (i.e., two arrays), the probability that a random sampling of the two sets of genes would result in any given set is the hypergeometric probability (designated "P(m)"). The hypergeometric probability essentially describes the probability of obtaining m common genes from two independent selections of entities of size $n_1$ and $n_2$ respectively, from a set of n entities. For the application to a microarray comparison involving X and Y number of genes in two arrays with M number of common genes between them, wherein x and y number of genes are chosen independently from the first array and second array and where x' and y' denote the number of genes in x and y respectively that are present in both arrays, the probability that x' and y' will have an overlapping gene set with in members is equal to p(m). Hypergeometric probability can be calculated from the following formula (Formula I) (where C(a,b)=a!/[b!(a−b)!]):

$$p(m) = \frac{C(x', m)C(M-x', y'-m)}{C(M, y')} = \frac{\binom{x'}{m}\binom{M-x'}{y'-m}}{\binom{M}{y'}}$$

However, the inventors have discovered that the hypergeometric distribution is sub-optimal in many cases for ascertaining an acceptably accurate probability of an overlap set being identified by chance from two distinct microarray experiments in which the genes constituting the two microarrays are not identical. Considering the expression for hypergeometric probability (above), it generally uses M which is the number of genes that the first array and the second array share in common, rather than the total number of genes in each of the two arrays. Generally speaking, as the total number of genes that the arrays share in common diverge (i.e., decrease), then the accuracy of the hypergeometric probability weakens, since the hypergeometric probability is a function of the number of genes that the arrays share (i.e., M), rather than the total number of genes of each array. Accordingly, the likelihood of making a Type I or a Type II error increases, in the case of Type II error, this phenomenon would result in an experimenter failing to reject a null hypothesis (such as; for example, "there are no differences between expression of genes under the two conditions of the experiment") associated with a given overlap set generated using data from two different arrays, thus failing to detect a statistically significant, overlap and accordingly failing to ascribe any biological significance to the observed overlap set. For many biological applications, for example, in determining gene signatures for a disease or disorder, the results can be devastating—even fatal, where a patient's diagnosis or prognosis relies on the accuracy of the overlap probability determination.

Thus, methods for determining overlap probability that do not rely on hypergeometric probability are provided. The methods as applied to microarray analysis include taking into account all of the genes of each microarray experiment, rather than only genes that two microarrays share in common. In the limiting case where the genes comprising the two arrays are identical, the overlap probability method can yield the same accuracy as the hypergeometric method. In other cases, especially when the number of genes shared between arrays is less than the number of genes in the smaller of the two arrays, the overlap probability method can provide higher statistical accuracy and thus in many instances decrease the likelihood of false negatives (or positives) in identifying statistically and/or biologically significant overlap sets.

Differences between the hypergeometric probability approach and the overlap probability approach can be illustrated by reference to FIG. 1. In FIG. 1, referring to the Venn diagram to the left of the figure, the big oval on the left represents the gene set of a first microarray and uppercase X refers to the total number of genes in this gene set, and the big oval on the right represents the gene set of a second microarray and uppercase Y refers to the total number of genes in this second microarray. Uppercase M represents the number of genes in common between two arrays. Cross-hatched lowercase x represents the size of a subset of genes (i.e., a subset of genes of interest in a microarray experiment) on the first microarray chip. Cross-hatched lowercase y represents the size of a subset of genes (i.e., a subset of genes of interest in a microarray experiment) on the second microarray chip (uppercase Y). The size of the intersection between the two cross-hatched is denoted as m, which is the same lowercase m as used in calculating hypergeometric probability and which represents an overlap of the subset of genes of interest of the first array and the subset of genes of interest on the second array. Thus, referring to the left diagram in FIG. 1, the overlap probability (i.e., the probability of drawing a lowercase m of a given size) includes consideration of the probability of drawing lowercase x elements from X multiplied by the probability of drawing lowercase y elements from Y.

Referring now to the right diagram of FIG. 1, which illustrates the parameters considered using the hypergeometric method, M is the number of genes common between the two arrays, x' is the size of a portion of the subset of genes of interest on the first microarray chip that are also present on the second microarray chip (this portion is the same as the intersection between the cross-hatched lower case x number of first subset genes from the first microarray and the M number of common genes between the two microarray chips, as shown on the left diagram of FIG. 1), y" is the size of a portion of a subset of genes of interest on the second microarray chip that are also present on the first microarray chip (this portion is the same as the intersection between the lower case y number of cross-hatched second subset genes from the second microarray and the M number of common genes between the two microarray chips, as shown on the left diagram of FIG. 1), and lowercase m represents the number of an overlap of the subset of genes of interest on the first microarray and the subset of genes of interest on the second microarray (i.e., the same m as employed in the overlap probability method). As seen from the right diagram of FIG. 1, the hypergeometric method does not consider draws from the total number of genes on each microarray chip, but instead considers only draws from the genes common to both microarray chips (i.e., draws from uppercase M number of genes). Thus, the hypergeometric distribution does not consider, in calculating probability of drawing a lowercase m of a given size, the probability of selecting a subset of genes from the total number of genes in either array, but only the probability of selecting x' or y' number of genes from the overlap genes (of size M) of both chips. Accordingly, in the case that the first microarray chip consists the same gene set as the second microarray chip, the probability of getting m number of overlap by random chance is the same by using either hypergeometric distribution or overlap probability calculation, because in this case X=Y=M, x'=x, and y'=y. However, in the cases where the two chips do not consist of the same gene set, the probabilities calculated from the two methods frequently are very different, with the overlap probability method being more accurate. As a result, highly inaccurate probabilities generated from hypergeometric distribution will very often result in false acceptance or rejection of null hypotheses.

Accordingly, the probability that an overlap set is selected by chance is given by the overlap probability p(m) which is given by the following formula (Formula II):

$$p(m) = \frac{C(M,m) \sum_{i=0}^{min(x-m,M-m)} [(C(M-m,i))(C(X-M,x-i-m))(C(Y-m-i,y-m))]}{(C(X,x))(C(Y,y))}$$

Referring to Formula II, X refers to the number of all genes of a first microarray chip; Y refers to the number of all genes of a second microarray chip; M refers to the number of genes common to the first microarray chip and the second microarray chip; lowercase x refers to the size of a subset of genes of interest on the first microarray chip; lowercase y refers to the size of a subset of genes of interest on the second microarray chip; m refers to the size of an overlap set formed by the genes of interest from the first microarray of size lowercase x and the genes of interest from the second microarray of size lowercase y: i refers to the number of genes of interest in the first array that are not included in the overlap set but are included in both arrays; C(M,m) refers to the number of possible ways of choosing m number of genes from the set of common genes between the two microarrays (with uppercase M number of genes); C(X,x) and C(Y,y) refer, respectively, to the number of possibilities of choosing lowercase x number of genes of interest from the first microarray (with uppercase X number of genes) and the number of possibilities of choosing lowercase y number of genes from the second microarray (with uppercase Y number of genes).

In short, the overlap probability considers all possible ways of drawing a first subset of genes of interest from a first microarray (i.e., all possible ways of selecting x from X) multiplied by ail possible ways of drawing a second subset of genes of interest from a second microarray (i.e., all possible ways of selecting y from Y). The overlap probability method employs the above consideration as denominator to provide a dividend (i.e., the overlap probability) when considered with a numerator that multiplies all number of ways of picking an overlap set of genes of interest from genes common to both arrays (i.e., all ways of drawing lowercase m from uppercase M) by a sum, over the minimum of either (a') the number of genes of the first subset of genes that are not common with the second subset of genes (i.e. x-m), or (b') the number of genes common between the two micros nays excluding the number of genes common between the two subsets of genes (i.e. M-m), of: (a") the number of ways of choosing genes in that part of the first subset of genes that are included in the second microarray but not in the overlap set from the number of common genes between the two microarrays excluding the overlap set (i.e., C(M-m,i), multiplied by (b") the number of ways of choosing that part of the first subset of genes that are not included in the second microarray, from the number of genes in the first microarray excluding the genes common with the second microarray (i.e., C(X-M, x-i-m)), multiplied by (c") the number of ways of choosing the number of genes in that part of the second subset of genes that are not in the overlap set from the number of genes in the second microarray excluding those genes in the first subset of genes (i.e., C(Y-m-i, y-m).

As can be seen from the formula and the explanation above, the overlap probability method can be distinguished from the hypergeometric probability in that the overlap probability method takes info account the total number of genes, uppercase X and uppercase Y, present on each of the microarrays. The overlap probability method does this by considering all possible ways of drawing a first subset of genes from a first microarray (i.e., all possible ways of selecting a subset of x number of genes from X number of genes in the first microarray) multiplied by all possible ways of drawing a second subset of genes of size y from a second microarray of size Y. This distinguishing feature of the overlap probability method represents a significant departure over the hypergeometric method.

Determining draw probabilities by taking into account the total number of genes on both microarray chips, without respect to whether genes are shared or not, increases the overall sample size for the selection of a subset genes. As a result, statistical accuracy is increased. Because statistical accuracy increases, the likelihood of falsely accepting or rejecting a null hypothesis decreases which in practice results in better inference of biological results.

Various aspects and embodiments employing overlap probability methods concerning applications to biological array analysis are presented below.

In one aspect, a computer-implemented method for analyzing data from two microarrays, comprising:

providing a first gene subset from a first microarray;

providing a second gene subset from a second microarray, wherein the first microarray and the second microarray comprise a different set of genes, and wherein the first gene subset and the second gene subset may or may not overlap (overlap size>=0);

determining the probability that the overlap set is drawn by chance, wherein the probability that the overlap set is drawn by chance comprises a function of the total number of ways of selecting the first gene subset from ail genes of the first microarray and comprises a function of the total number of ways of selecting the second gene subset from all genes of the second microarray.

In one embodiment, wherein the probability that the overlap set is selected by chance comprises a dividend of the number of ways of selecting the overlap set from all genes common to both the first microarray and the second microarray, divided by: (a) the number of ways of selecting the first gene set from the first microarray, multiplied by (b) the number of ways of selecting the second gene set from the second microarray.

In another embodiment, the number of ways of selecting the overlap set of ail genes common to both the first microarray and the second microarray multiplied by a sum, over the minimum of either (a') the number of genes of the first subset of genes that are not common with the second subset of genes, or (b') the number of genes common between the two microarrays excluding the number of genes common between the two subsets of genes, of: (a") the number of ways of choosing genes in that part of the first subset of genes that are included in the second microarray but not in the overlap set, from the number of common genes between the two microarrays excluding the overlap set, multiplied by (b") the number of ways of choosing that part of the first subset of genes that are not included in the second microarray, from the number of genes in the first microarray excluding the genes common with the second microarray, multiplied by (c") the number of ways of choosing the number of genes in that part of the second subset of genes that are not in the overlap set, from the number of genes in the second microarray excluding those genes in the first subset of genes.

In another embodiment, the overlap probability is determined by the following formula (Formula II):

$$p(m) = \frac{C(M, m) \sum_{i=0}^{min(x-m, M-m)} [(C(M-m, i))(C(X-M, x-i-m))(C(Y-m-i, y-m))]}{(C(X, x))(C(Y, y))}$$

wherein:

X is the total number of entities in the first array;

Y is the total number of entities in the second array;

M represents the number of entitles common to both the first array and the second array;

m is the number of entities in the overlap set;

x is the number of entities of the first entity subset;

y is the number of entities of the second entity subset; and, p(m) is the probability of selecting the overlap set by chance.

In various embodiments, the entities are selected from genes, proteins, ligands, and antibodies.

In one embodiment, X represents the total number of genes of a first gene array and Y represents the total number of genes of a second gene array.

In one embodiment x and y represent the number of genes in gene sets. In another embodiment, x and/or y denote the size of sets of genes that are differentially expressed in a disease or a disorder. In comparison to a sample from an individual who is not afflicted with the disease or disorder. In another embodiment, x and/or y represent the size of sets of genes whose differential expression are a prognostic indicator for a disease or disorder. In another embodiment, x and/or y represent the size of sets of genes of an individual treated with a selected pharmaceutical substance, and the expression level of these genes are indicative of the efficacy of the selected pharmaceutical substance in treating a disease or a disorder. In another embodiment, x and y represent the size of sets of genes having one or more single nucleotide polymorphisms. In another embodiment, x and/or y represent the size of sets of genes that identify a genotype or a haplotype. In another embodiment, x and/or y represent the size of sets of genes that identify an individual to the exclusion of other individuals in a defined population. In another embodiment, x and y represent the number of genes that are commonly regulated by a cytokine.

In one embodiment, the overlap set represents a set of genes employed as a prognostic indicator. In another embodiment, the overlap set represents a set of genes that comprise an expression signature for a disease or a disorder. In another embodiment, the overlap set represents a set of genes that is pharmacogenomic signature, for example, an expression pattern of cell from a human subject that indicates suitability or unsuitability in responding to a therapeutic treatment with an approved pharmaceutical. In another embodiment, the overlap set represents a set of genes common to two biological pathways, for example, an inflammatory pathway and a cytokine regulation pathway.

In one embodiment, the first gene subset and the second gene subset are independently selected from the group consisting of genes differentially regulated in a disorder, genes differentially regulated in development, genes differentially regulated between individual samples being assayed.

In one embodiment, the array is a gene array and the first array and the second array differ by at least 1% of the total number of genes of the first and the second array. In another embodiment, the first array and the second array differ by at least 10% of the total number of genes of the first array and the second array. In another embodiment, the first array and the second array differ by at least 20% of the total number of genes of the first array and the second array. In another embodiment, the first array and the second array differ by about 10%, about 20%, about 30%, about 40%, about 50%, about 60%, about 70%, about 80%, or about 90% of the total number of genes of the first array and the second array.

In another aspect, a computer program product is provided, comprising a computer-readable medium comprising instructions encoded thereon for carrying out a method as described herein. In various embodiments the computer program product enables a computer having a processor to determine an overlap probability as described herein. In various embodiments, the computer program product is encoded such that the program, when implemented by a suitable computer or system, can receive all parameters necessary to determine an overlap probability (see Formula 2) and return at least one overlap probability value.

In another aspect, a computer system for determining overlap probability is provided, wherein the system comprises a processor and memory coupled to the processor, and wherein the memory encodes one or more computer programs that causes the processor to determine an overlap probability. In various embodiments, the memory encodes one or more computer programs that cause the processor to determine a least significant overlap (i.e., Critical Overlap Size, or $m^{COS}$, for a given statistical significance S) or a cumulative overlap probability.

In one embodiment, the memory comprises instructions for determining overlap probability in accordance with Formula II.

The computer software product may be written using any suitable programming language known in the art. System components used with the invention may include any suitable hardware known in the art. Suitable programming language and suitable hardware system components, include those described in the following U.S. Pat. No. 7,197,400 (see, e.g., cols. 8-9), U.S. Pat. No. 6,691,042 (see, e.g., cols. 12-25); U.S. Pat. No. 8,245,517 (see, e.g., cols. 16-17); U.S. Pat. No. 7,272,584 (see, e.g., col. 4, line 26-col. 5, line 18); U.S. Pat. No. 8,203,987 (see, e.g., cols. 19-20); U.S. Pat. No. 7,386,523 (see, e.g., col. 2, line 26-col. 3, line 3; see also, col. 8, line 21-col. 9, line 52); U.S. Pat. No. 7,353,116 (see, e.g., col. 5, line 50-col. 8, line 5), U.S. Pat. No. 5,985,352 (see, e.g., col. 31, line 37-col. 32, line 21).

In one embodiment, the computer system that is capable of executing the computer-implemented methods herein comprises a processor, a fixed storage medium (i.e., a hard drive), system memory (e.g., RAM and/or ROM), a keyboard, a display (e.g., a monitor), a data input device (e.g., a device capable of providing raw or transformed microarray data to the system), and optionally a drive capable of reading and/or writing computer-readable media (i.e., removable storage, e.g., a CD or DVD drive). The system optionally also comprises a network input/output device and a device allowing connection to the internet.

In one embodiment the computer-readable instructions (e.g., a computer software product) enabling the system to calculate an overlap probability as described herein (i.e. software for calculating a probability according to Formula 2) are encoded on the fixed storage medium and enable the system to display the overlap probability to a user, or to provide the result of an overlap probability to a second set of computer-readable instructions (i.e., a second program), or to send the overlap probability to a data structure residing on the fixed storage medium or to another network computer or to a remote location through the internet.

In one embodiment the system is capable of receiving microarray data directly from a microarray reader functionally linked to the system. Functional linkage refers to the ability of the microarray reader to send microarray signal data, or transformed microarray signal data, in a computer-readable form to the system. In this embodiment, the system further comprises any suitable microarray software known in the art for manipulating raw microarray data. Suitable software for manipulating raw microarray data includes, for example, software capable of correcting or normalizing microarray data, building a data structure of transformed microarray data, and/or placing microarray data in a format suitable for input into the overlap probability software described herein. By way of example and not by way of limitation, suitable software includes GeneChip™ software, GeneSpring™ software, and Resolver™ software.

In one aspect, a microarray analysis system is provided, comprising a microarray reader functionally linked to a computer system comprising an input/output device capable of receiving data from the microarray reader, a processor, a fixed storage medium, and connectivity to a network and/or the internet, wherein on the microarray reader or on fixed storage medium (in physical proximity to the system or accessible through a network or the internet) is at least one computer software product for transforming raw microarray data (e.g., normalizing and error-correcting raw microarray data) and at least one computer software product for calculating an overlap probability as described herein from the transformed (e.g., normalized and/or corrected) microarray data.

Suitable microarray readers include those capable of detecting one or more fluorescence signals and converting the signals to a suitable data format, for example, signal intensity. Examples of microarray readers include Agilent's DNA Microarray Scanner (optionally with Feature Extraction Software™); Asymetrix's GeneChip™ Array Station or GeneChip™ Scanner 3000; Axon GenePix™ 4000 series scanners; ArrayWorx™ biochip and microarray scanners; GeneFocus DNAscope™ scanners; Genomic Solutions GeneTAC™ scanners; Packard Biosciences Scan Array® series scanners; Virtek Visions' ChipReader™ scanners; ArrayIt InnoScan™ scanners.

The systems can comprise software products for transforming microarray data info convenient forms or data structures, and writing the transformed data or data structures to a computer-readable medium, such as, for example, GeneSpring™, Resolver™, Oncomine™, Able Image Analyzer™, AIDA Array Metrix™, ArrayFox™, ArrayPro Analyzer™, ArrayVision™, Dapple, F-scan. GenPix™, GeneSpotter™, GridGrinder, ImaGene™, Iconoclust™, IPlab Microarray Suite™, Lucidea Automated Spotfinder™, Matarray, Phoretix™, P-scan™, QuantArray™, ScanAlyze, Spot, SpotReader, TIGR Spotfinder, and USCF Spot.

In various embodiments, methods, computer program products, and systems for determining a least significant overlap (i.e., Critical Overlap Size, or $m^{COS}$, for a given statistical significance S) of two microarray studies are provided. Methods for determining the least significant overlap (Critical Overlap Size) return the size of the smallest overlap set that is statistically significant, given a set of parameters associated with two studies.

Figure 4:
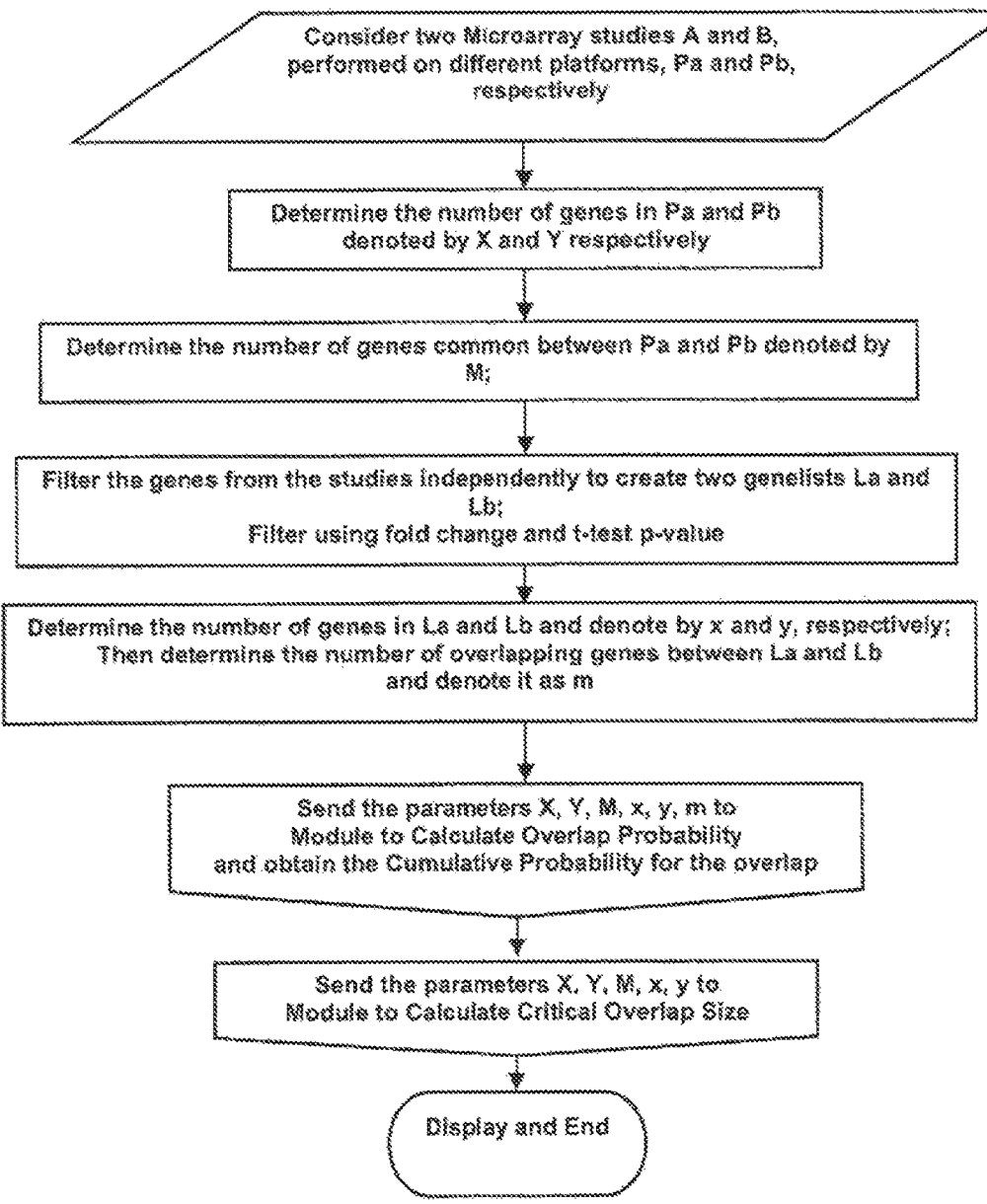
FIG. 4 illustrates an embodiment of a computer-implemented method for determining Critical Overlap Size of two gene signatures each from a microarray study and the probability of the overlap using an overlap probability method.

FIG. 4 illustrates a graphical representation of method for calculating least significant overlap (i.e., Critical Overlap Size) between two studies (Study A and Study B) of microarray data. In the embodiment illustrated, the two microarray studies are carried out on two different microarray platforms ("Pa" and "Pb"). X and Y parameters are assigned the values of the number of genes on each platform. M is assigned the value of the number of genes common between Pa and Pb. If necessary, genes can be mapped across the platforms (and/or across species) using a suitable linking identifiers such as, for example, Unigene or Homologene; and tools such as available in GeneSpring™, Resolver™.

Gene lists (i.e., subsets of genes of interest from each microarray) are then prepared from each platform. Gene list La is created from Study A using platform Pa, and gene list Lb is created from Study B using platform Pb by independently filtering genes in each study using a suitable filtering technique. Any suitable filtering technique known in the art can be used. In one embodiment, the suitable filtering technique employs fold-change and t-test p-value, and the filtering technique used to generate La is the same filtering technique used to generate Lb.

The number of genes in La and Lb are determined and assigned to x and y. The number of overlapping genes between La and Lb is determined and assigned to m.

Parameters X, Y, M, x, y, and m are used to calculate overlap probability and to obtain the cumulative probability for the overlap. The least significant overlap, or Critical Overlap Size, is also determined.

In various embodiments, methods, computer program products, and systems for determining a cumulative overlap probability for an overlap set two microarrays is provided. Methods for determining the cumulative overlap probability return the cumulative probability (as measured by the area under the m vs. p(m) curve) associated with an m of a given size provided for a set of parameters for two microarrays.

Figure 5:
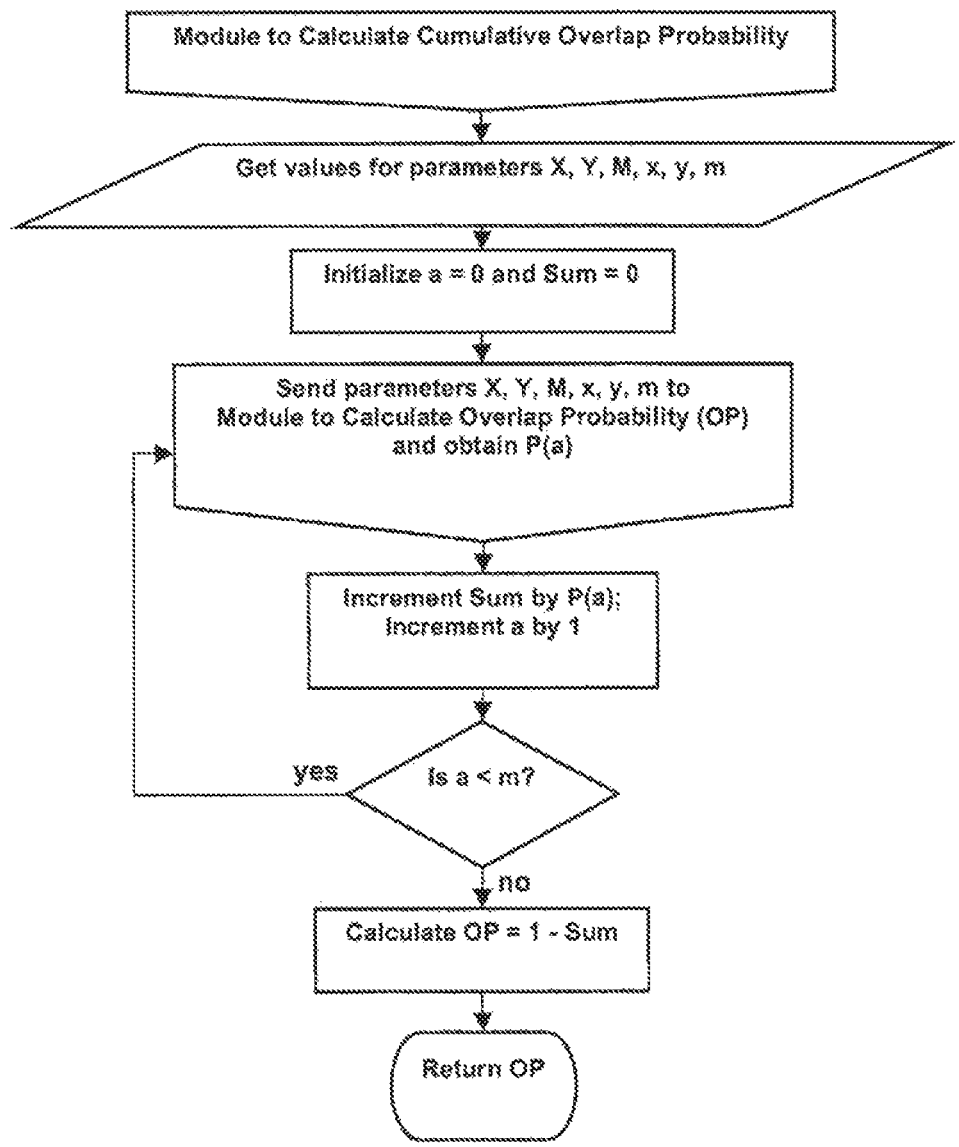
FIG. 5 illustrates an embodiment of a computer-implemented method for determining cumulative overlap probability.
Figure 6:
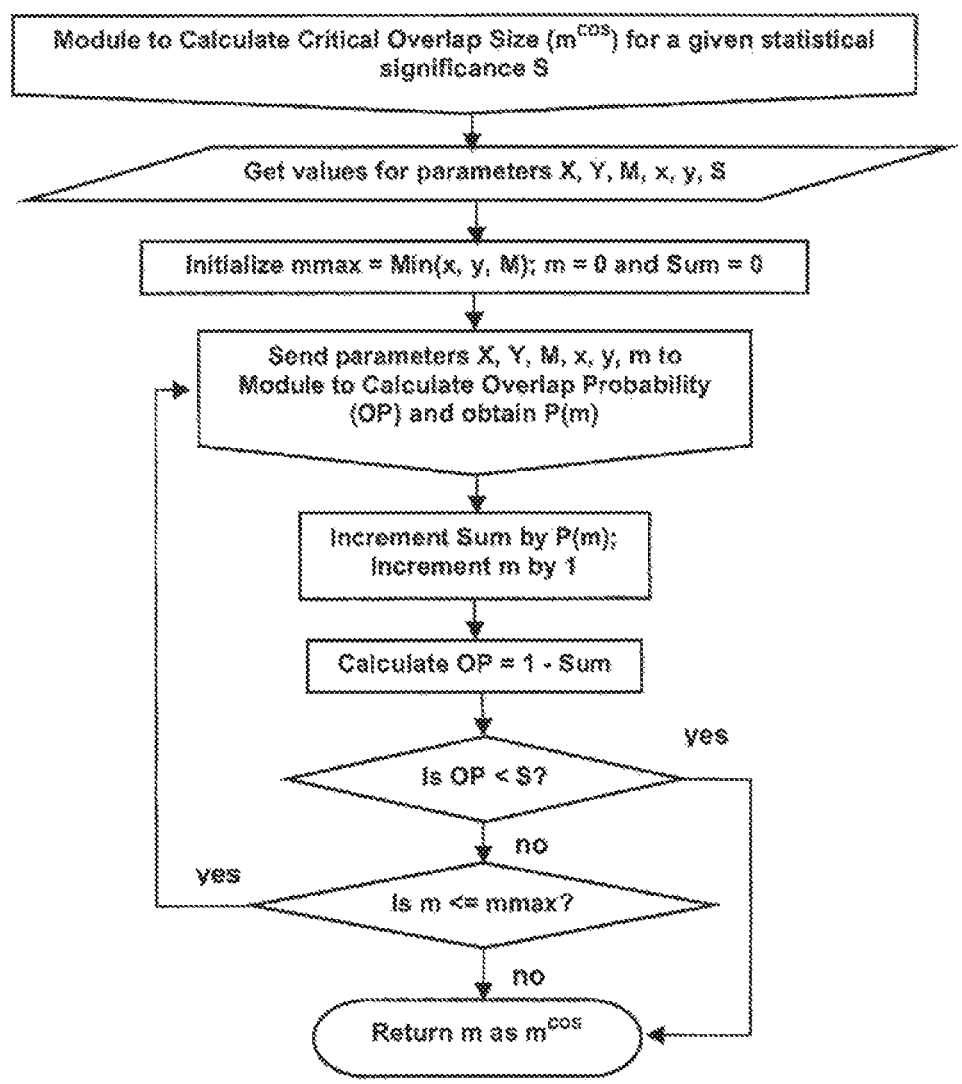
FIG. 6 illustrates an embodiment of a computer-implemented method for determining Critical Overlap Size using an overlap probability method.

FIG. 5 illustrates one embodiment of a computer-implemented method for determining cumulative overlap probability. In this embodiment, the software program receives values for parameters X, Y, M, y, and m. The program initializes a=0, and Sum=0. The parameters are then sent to a module for calculating overlap probability, iterating from a=0 to the value of the parameter (m−1) (i.e., the size of the overlap group minus one) to determine overlap probability for each value of a. When the size of the overlap group is reached (i.e., m is attained), the cumulative overlap probability is determined by adding the overlap probability values (from a=0 to a=m−1) and then subtracting this sum from 1, and displayed. Alternatively, the cumulative overlap probability can be calculated as the sum of the overlap probabilities obtained by varying a from m to the minimum of (x,y,M). However, this might take a lot of time to calculate when the parameters involved are large numbers, which as an example is typical with microarrays.

In another embodiment, a computer-implemented method for determining the Critical Overlap Size ($m^{COS}$) with a specified statistical significance (i.e. p-value; e.g., 0.05) is provided. FIG. 8 illustrates one embodiment for a software program that calculates the Critical Overlap Size with a specific significance level of cumulative overlap probability. In this embodiment the program receives values for parameters X, Y, M, x, y and S and initializes $m_{max}$ as the least of x, y, and M, m=0 and Sum=0. The program sends the parameters to a module or set of steps for calculating cumulative overlap probability (or overlap probability which in general is less desired to the cumulative value), iterating from m=0 to the value of the parameter $m_{max}$, and obtains p(m) for each value. The cumulative overlap probability at each m is determined until a cumulative overlap probability of less than S is reached, and the m value (size of overlap) is returned for the p(m) that falls below S. The stringency of the p-value (S) can be varied and 0.05 is a typical example.

In various embodiments, methods, computer program products, and systems for determining overlap probability for two microarrays having a non-identical set of genes are provided. Methods for determining the overlap probability return a p-value for a given overlap set m, given a set of parameters associated with two microarrays.

Figure 7:
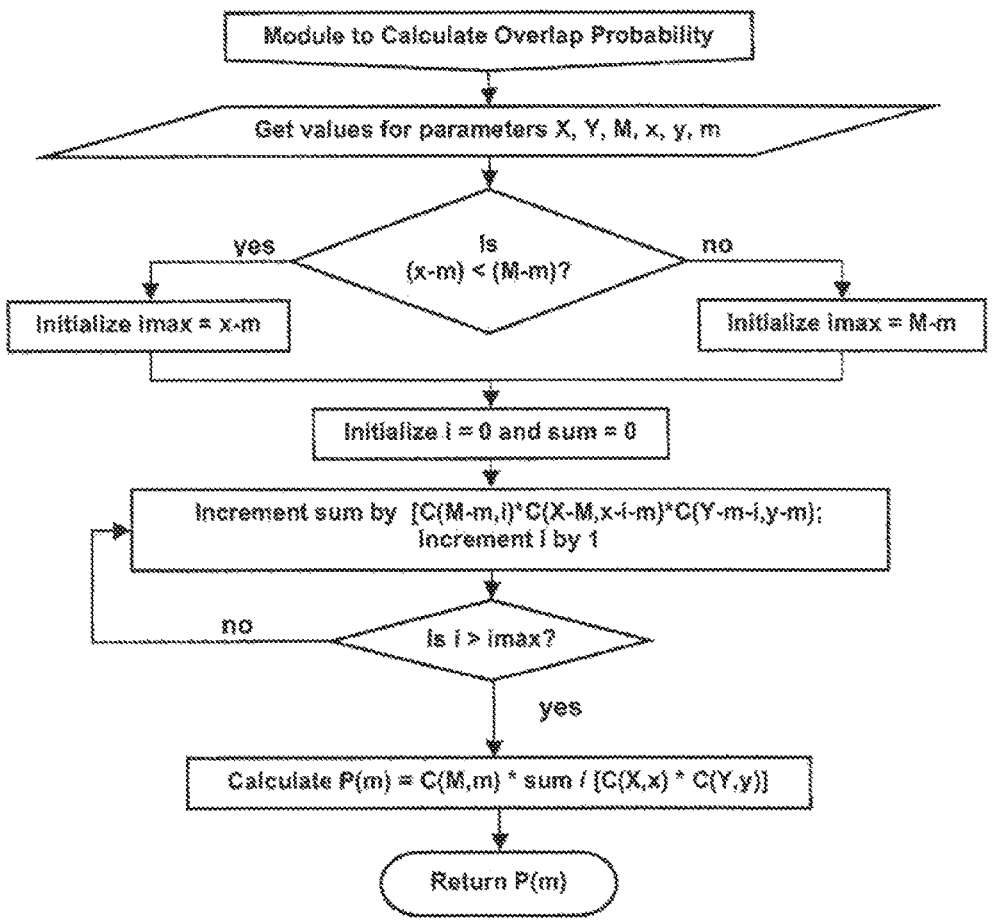
FIG. 7 illustrates an embodiment of a computer-implemented method for determining overlap probability.

FIG. 7 illustrates one embodiment of a computer-implemented method for determining overlap probability. In this embodiment, the software program receives values for parameters X, Y, M, x, y, and m. The number of iterations is determined, i.e., If (x-m)<(M-m), then iterations are (x-m); if (x-m)≥(M-m), then iterations are (M-m). The program then sums over the iterations the product of $(C(M-m) \cdot C(X-M, x-i-m) \cdot C(Y-m-i, y-m))$ until maximum iteration is achieved, after which it calculates P(m), given by $C(M,m) \cdot sum/[C(X,x) \cdot C(Y,y)]$. Finally, if returns (e.g., displays) the overlap probability P(m).

Overlap probability as determined by the formula described herein agreed well with overlap probability determined by an iterative simulation for two exemplary microarrays of 10 and 11 genes (see Example 1). Accordingly, the overlap probability formula provides an accurate determination of overlap probability.

When the overlap probability formula is employed with published microarray data (i.e., with actual gene lists, or gene subsets), it compares excellently with a Simulation employing the same published microarray data (see Examples 2 and 4).

Comparison of the overlap probability formula and the hypergeometric probability formula, using published microarray data, demonstrated that under certain circumstances, the hypergeometric probability greatly underestimates that significance of observed overlap sets (see Example 3).

The methods, computer products, and systems described herein can be used to analyze any microarray data for which an overlap set is obtained and wherein knowledge about the statistical significance of an overlap set is desired. Examples include, but are not limited to, those described below.

In one example, the methods, products, and systems can be used to analyze microarray experiments for comparing two sets of signature genes for a disease or a disorder (e.g., a particular gene subset of interest x and a particular gene subset of interest y) determined by any method in the art. The overlap probability can assist in determining whether the overlap set defines a signature for a disease or a disorder with a given level of statistical significance.

In another example, two arrays of antibodies or binding fragments or elements thereof exposed to a sample comprising an antigen or hapten, wherein the antigen or hapten is labeled or exposed to a labeled binding protein in a sandwich-type assay, can be analyzed to determine whether the overlap set contains a statistically significant group of antibodies associated with specific antigens. This method can be employed to determine phenotypic differences between samples, e.g., between normal and diseased cells, or between cell types.

In another example, two protein arrays can be exposed to one or more samples comprising antibodies or binding fragments or elements thereof, or ligands, wherein binding to the array can be directly or indirectly detected, and the results can be analyzed with the methods herein to determine the statistical significance of an overlap set of proteins associated with antibodies or ligands. If the samples are independently selected, a statistically significant overlap set can be used to determine what antibodies or ligands the individual samples share. This method can be used to determine phenotypic differences reflected by antibody or ligand repertoires between individuals.

In another example, two arrays of polynucleotides can be exposed to samples comprising genes with mutations or single nucleotide polymorphisms (i.e., SNPs), wherein the arrays comprise genes or gene segments that identify the SNPs and provide a genotype, and an overlap set can be examined to determine whether the samples are related, e.g., to determine consanguinity or identity, and at what statistical significance using a method as described herein.

In another example, two microarray studies can be compared to determine the statistical significance of overlapping disease gene lists, for example, as shown in Example 2, the significance of overlap disease genes lists from systemic juvenile idiopathic arthritis (SJIA) and rheumatoid arthritis (RA) studies. The existence of a significant overlap between the two studies provides evidence that SJIA and RA may result from defects or disorders in similar pathways, and that a therapeutic intervention effective against one disorder (e.g., SJIA) is likely to be effective against the other disorder (e.g., RA). In this example, SJIA patients can be assigned to a clinical trial for treatment with an agent that is effective against RA. Conversely, RA patients can be assigned to a clinical trial for treatment of an agent that is effective against SJIA.

Accordingly, a method for determining the likelihood that a treatment for a disorder will be effective is provided. The method comprises determining the overlap of a first gene list which registers the drug effect by comparing expression profiles of samples before and after treatment from a group of patients that is effectively treated with a pharmaceutical effective composition; and a second gene list which registers another disease by comparing the second disease samples with normal controls, using Formula 2; wherein if Formula 2 indicates that the overlap group is statistically significant, second group of patients can be a good indication for a clinical trial with the pharmaceutical effective composition.

For example, expression profiling studies of normal subjects compared with subjects having oral cancer revealed a subset of genes whose expression is elevated in oral cancer. See, U.S. Pat. No. 7,108,989. Comparing an expression profile of a subject with oral cancer with an expression profile of a subject who has not been diagnosed with oral cancer, and determining an overlap in elevated expression for the subset of genes whose expression is elevated in oral cancer can be carried out. Identification of an overlap set of overexpressed genes, and obtaining the probability of obtaining such an overlap set by chance as measured by the methods described herein, can assist a clinician in determining the likelihood that the test subject has oral cancer.

In another example, prognostic indicators comprising microarray signatures have been determined from populations of subjects having breast cancer. See, van de Vijver et al. (2002) A Gene-expression Signature as a Predictor of Survival in Breast Cancer, N. Eng. J. Med. 347/25:1999-2009. The gene expression signatures were a more powerful predictor of outcome in young patients with breast cancer than were existing systems based on clinical and histological criteria.

At least one clinical study (the "Microarray in Node Negative Disease may Avoid ChemoTherapy" trial) has been implemented to provide definitive evidence concerning a 70-gene prognostic expression signature in breast cancer in order to assign patients to treatment groups based on gene expression signatures. See, e.g., Bogaerts et al. (2008) Gene signature evaluation as a prognostic tool, challenges in the design of the MINDACT trial. Nat. Clin. Pract. Oncol. 3/10:840-551; see also, Cardoso et al. (2008) Clinical application of the 70-gene profile: the MINDACT trial, J. Clin. Oncol. 26/5:720-35.

Although the above examples address breast cancer, microarray signatures have been found, and are being developed, for a variety of diseases such as, for example, cancers of the prostate, lung, ovaries, bladder, lymphoma, medulloblastoma, glioma, acute myeloid leukemia, etc. (see, e.g., Glinsky et al. (2005) J. Clin. Invest. 115/6; 1503-1521. A person of skill would recognize that the methods, software, and systems described herein can also be applied to these signatures); early-stage esophageal adenocarcinoma (see, e.g., Oh et al. (2007) Molecular signature of esophageal adenocarcinoma derived from microarray analysis of paraffin-embedded specimens predicts systemic recurrence following resection. J. Clin. Oncol. 25/185(Supplement): 4563 (Abstract, 2007 ASCO Annual Meeting Proceedings (Post-Meeting Edition)).

Clinically useful molecular phenotyping using microarrays is not limited to cancer. Such phenotypes have been identified in other diseases or disorders, e.g., atherosclerosis (see, e.g., Seo et al. (2004) Gene Expression Phenotypes of Atherosclerosis, Arterioscler, Thromb. Vasc. Biol. 24:1922-1927.

Thus, identification of a prognostic signature in a patient would identify those patients who would benefit from further treatment in order to reduce the likelihood of mortality due to, e.g., undertreatment. The methods described herein can be used to accurately determine the overlap probability between an expression profile of a reference breast cancer subject in a good or a poor prognosis group and a test breast cancer subject with an undetermined prognosis. The methods provided herein would provide an accurate measure of statistical significance of the overlap group (e.g., a common prognostic signature).

Microarray analysis in clinical medicine, genotyping, and phenotyping has a well-established utility. The ability to accurately determine the statistical significance of an overlap group (e.g., generated to test for a disease or prognostic signature) when analyzing microarray studies from nonidentical platforms enhances reliability and thus enhances the well-established utility of microarray studies in the clinical context.

The methods and systems described herein are not limited to microarray analysis, but is generally applicable to determining the probability of obtaining an overlap set of a given size from two subsets of entitles independently drawn without replacement from two entity sets, whatever type of data the two entity sets comprise.

In one example unrelated to microarray analysis, the methods and systems can be used to reveal a possible relationship between two sets of sociological data that are not obviously related. For example, a first study assesses all male minors in community C (representing X in Formula 2) describes the number of male minors of community C using illegal drugs (representing x in Formula 2); and a second study assesses all persons in high-income households in community C (representing Y in Formula 2), ascertains the number of such persons using illegal drugs (representing y in Formula 2), The number of male minors in community C from high-income households (representing M in Formula 2) and the number of male minors using drugs in high income families in community C (representing m in Formula 2) can be used to calculate the significance of the overlap group (m, the number of male minors using drugs in high income families in community C). If m is significant, then there is likely to be a relationship between the use of drugs and family income in male minors in community C.

Accordingly, methods, software, and systems for determining overlap probability of two nonidentical studies are also provided.

EXAMPLES

The following examples are included to provide those of skill in the art how to make and use the methods and compositions described herein, and are not intended to limit the scope of what the inventors regard as their invention.

Example 1: Overlap Probability by Formula Compared with Overlap Probability Determined by a Simulations An illustrative simulation was performed in which p-values generated by an iterative simulation were determined and compared with the output of the overlap probability formula described herein. This simulation illustrated that p-values generated by the simulation are quite similar to p-values generated using the overlap probability formula. The simulation was performed for a simple case for a first entity set comprised of X number of entities and a second entity set of size Y, where the two entity sets have a common set of entities of size M. A subset entity of size x is chosen from the first entity set and a subset entity of size y is chosen from the second entity set, where the number of entities in common between the subsets is represented by m. Briefly, for step 1, the protocol arbitrarily chooses fixed values of X, Y, M, x, and y (X>=x; Y>=y, X>=M; Y>=M); for step 2, entity sets of size X and Y with an overlap of size M were generated randomly; for step 3, the simulation performed random picks of x number of entities from first entity set, and y number of entitles from second entity set, determining an m for each pair of picks. Step 3 was repeated a large number of times (about $10^8$ iterations), and the value of m was recorded for each repetition. This protocol was carried out for low values of X, Y, M, x and y in order to obtain results for all values of m. Average p-values from three simulation runs each with $10^8$ iterations are shown in Table I for this simulation, where X=10, Y=11, M=7, x=3, and y=4.

TABLE I

| | Illustrative Example of Overlap Method p-value | |
| --- | --- | --- |
| m | Overlap Method | Simulation (Average) |
| 0 | 0.3820202 | 0.382028233 |
| 1 | 0.4793939 | 0.479371833 |
| 2 | 0.1315151 | 0.131523633 |
| 3 | 0.0070707 | 0.0070763 |
| >4 | 0 | 0 |

The illustrative simulation reveals that the overlap probability formula accurately estimated the overlap probability as compared to a simulation.

Example 2: Overlap Probability Simulation with Microarray Data

Overlap probability was determined in a simulation using actual microarray data. Data generated by an Asymetrix U133Plus Chip™ (Fall N, et al. (2007) Arthritis Rheum. 58(11):3793-804) and an Invitrogen GF211 Chip™ (Liu, Z. et al. (2008) Hum Mol Genet. 15(3):501-9.) were subjected to a simulation protocol. The protocol took more than 578 hours to complete on an Intel Xeon™ 2.8 Ghz processor running in a cluster having a total memory of 2 GB. Data for each chip were obtained from peripheral blood mononuclear cells of patients provided through the NCBI GEO database.

Fall et al. studied gene expression profiles of patients with Systemic Juvenile idiopathic Arthritis (SJIA) (the "SJIA Study"). An analysis of the SJIA study revealed a set of 805 genes that were significant and differentially expressed (upregulated) in SJIA as compared to normal patients (column x in Table 2).

Liu et al. studied expression profiles of various auto immune diseases including Rheumatoid Arthritis (RA), Early Rheumatoid Arthritis (ERA), Type I diabetes/insulin-dependent diabetes mellitus (IDDM), Systemic Lupus Erythematosus (SLE), and Multiple Sclerosis (MS) (the "Autoimmune Study"). The Autoimmune Study contained two groups of controls containing healthy individuals with or without any family history of autoimmune disease Controls without a family history of autoimmune disease were considered similar to the analysis with the SJIA data (i.e., "normal" individuals from the different studies were considered equivalent for control purposes).

A pairwise analysis was performed for each disease group against controls and gene lists with significantly unregulated genes were identified. The number of genes obtained for each disease type is listed in Table 2, column y. The SJIA genelist was then compared, pairwise, with each genelist from the Autoimmune Study and the overlap determined. The cumulative-value ($p^c$) for the overlap was calculated using the hypergeometric probability method (HG) and the overlap probability method (OP). Results are shown in Table 2.

TABLE 2

Overlap Probabilities between SJIA Genelist and Autoimmune Disease Genelists

| | x | y | x' | y' | m | $p^c$ (OP) | $p^c$ (HG) |
|---|---|---|---|---|---|---|---|
| SJIA vs. RA | 805 | 329 | 236 | 312 | 38 | 3.55E−15 | 0.000172 |
| SJIA vs. ERA | 805 | 500 | 236 | 479 | 43 | 1.67E−12 | 0.026989 |
| SJIA vs. IDDM | 805 | 408 | 236 | 393 | 39 | 7.06E−13 | 0.007471 |
| SJIA vs. MS | 805 | 437 | 236 | 420 | 41 | 3.34E−13 | 0.008079 |
| SJIA vs. SLE | 805 | 214 | 236 | 207 | 22 | 1.97E−08 | 0.020843 |

HC = hypergeometric probability
OP = overlap probability

Results revealed that p-values determined by the overlap probability method indicated a highly significant overlap between the SJIA Study and each of the Autoimmune Study gene lists. In contrast, the hypergeometric probabilities for the same comparisons were many orders of magnitude less significant. Further, among the overlapping genes (ranging from 22 to 43), 13 were common in all five comparisons, and 35 genes occurred in a majority of them. These overlapping genes were then submitted to Ingenuity Pathway Analysis™ (Ingenuity Systems, Inc., Redwood, Calif.) in order to determine if they shared any common pathways, to assist in exploring any apparent biological basis for the significant overlap. Ingenuity Pathway Analysis™ revealed that the overlapping genes share many genes in the interleukin and TNF pathways (data not shown).

Example 3: Comparison of Overlap Probability and Hypergeometric Probability Methods The SJIA Study and the Autoimmune Study were used to compare the overlap probability and hypergeometric probability methods. First, a standard protocol was used to analyze the datasets independent from the probability comparison A Student's t-test with Benjamini-Hochberg correction was performed. Genes having a p-value of less than 0.1 were chosen, and gene lists were formed by those genes that were upregulated 1.5-fold or more in the diseased group as compared to the control group. Probe IDs of the resulting genelist genes were translated to Unigene IDs in order to facilitate comparison across platforms. Microarray analysis and translation were performed using GeneSpring GX 7.3™ (GeneSpider updated Dec. 12, 2007). The number of unique Unigene IDs that resulted from the translation was 30,877 for the U133Plus Chip™ (X) and 3,690 for the GF211 Chip™ (Y). Common genes between the two chips were numbered at 3,489 (M). The number of genes of interest representing the SJIA signature on the U133Plus Chip™ was 805 (x) of which 236 (x') were also on the GF211 Chip™. The number of genes of interest representing the RA Signature on the GF211 Chip™ was 329 (y) of which 312 (y') were also present on the U133Plus Chip™. Using these parameters, overlap probability and hypergeometric probability were determined. Results are shown in Table 2 (Example 2).

The microarray data of the SJIA Study and the Autoimmune Study were subjected to comparisons in which p-values determined by the overlap probability method as described herein were compared with p-values determined by the hypergeometric distribution method using SJIA data and RA data. In the first comparison, the parameters selected were X=30,877, Y=3,690, M=3,489, x=805, y=329, x'=236, and y'=312 (see line 1, Table 2), with m varied from 0 to 329. The resulting plot is shown in FIG. 2.

Figure 2:
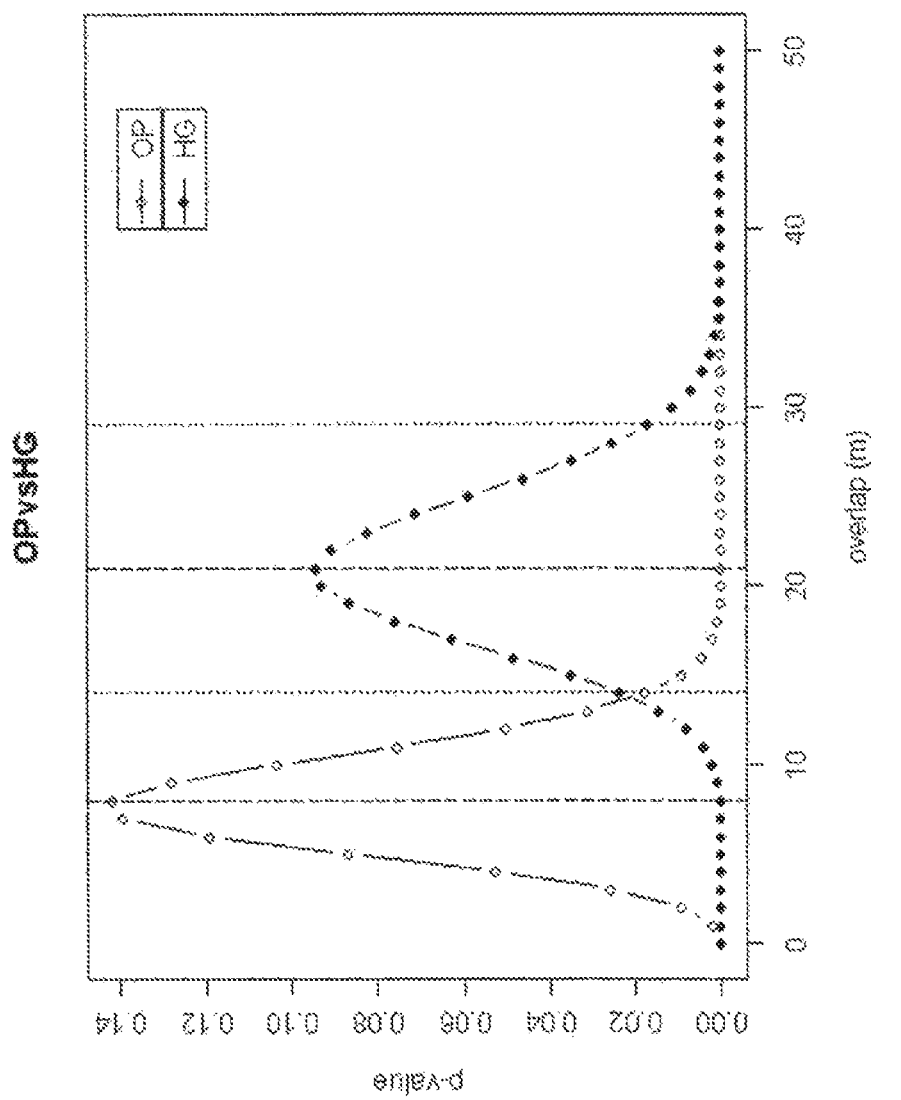
FIG. 2 illustrates a comparison between overlap probability (left curve; open circles) and hypergeometric probability (right curve; closed circles).

In FIG. 2, the peak of the curve (overlap probability at left, hypergeometric probability at right) represents the mean overlap of the corresponding distribution. The mean of the hypergeometric probability (HG) distribution is known to be given by:

$$\text{Mean}^{HG} = M(x'/M)(y'/M)$$

The mean of the overlap probability (OP) distribution can be calculated by.

$$\text{Mean}^{OP} = M(x/X)(y/Y)$$

Values of the overlap set (m) at a p value of 0.05 ($m^{0.05}$) are depicted as vertical lines in FIG. 2, as derived from cumulative p-values. The $m^{0.05}$ value defines the minimum number of overlapping genes that is statistically significant. The overlap probability method identifies the $m^{0.05}$ (i.e. $m^{COS}$ at S=0.05) at an overlap set of 14, whereas the hypergeometric distribution requires an overlap set of at least 29 genes for a p value of 0.05 ($m^{0.05}$). Thus, the hypergeometric distribution in this example greatly underestimates the significance of the overlap set between SJIA and RA overlap.

Figure 3:
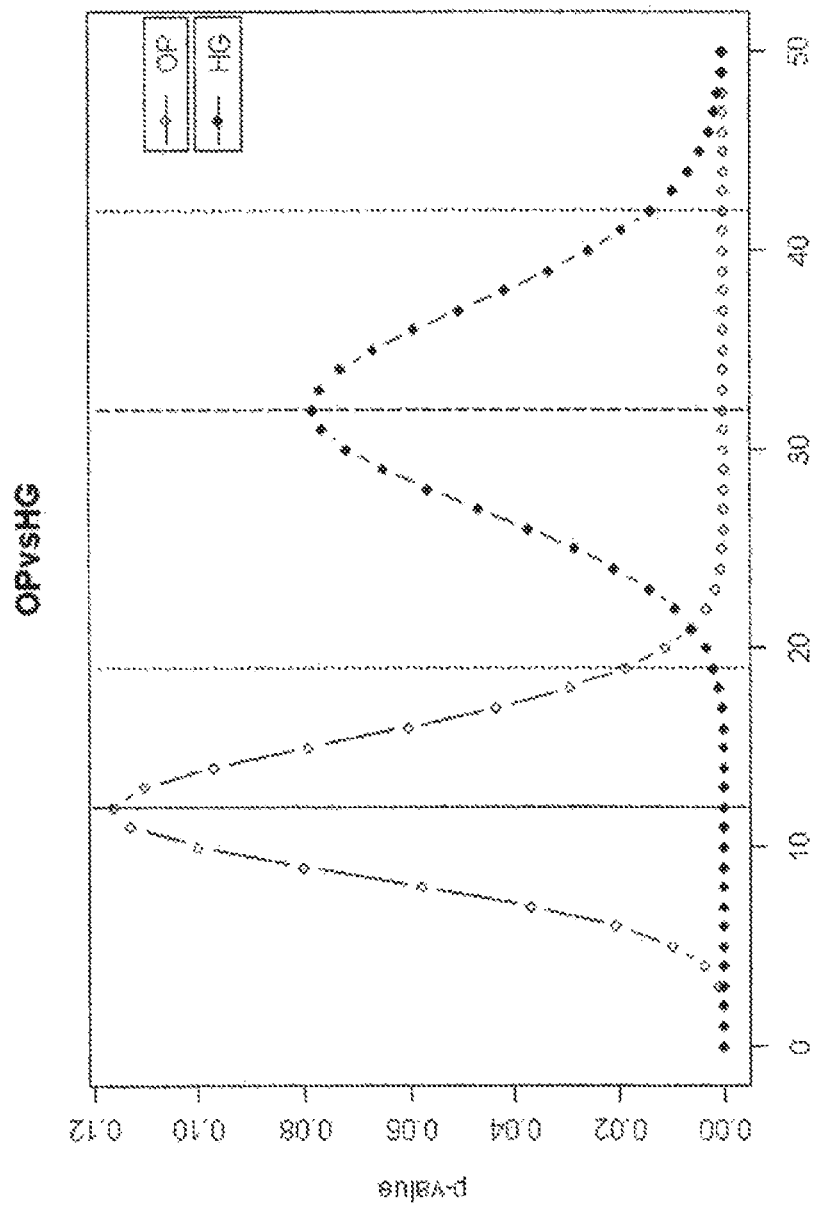
FIG. 3 illustrates a comparison between overlap probability (left curve; open circles) and hypergeometric probability (right curve; closed circles).

A similar comparison was performed for the overlap gene set of the SJIA and ERA gene lists. The parameters used for the SJIA vs. ERA comparison were X=30,887, Y=3,690, M=3,489, x=805, y=500, x'=236, y'=479 (line 2, of Table 2), varying m from 0 to 500. The resulting plot is shown in FIG. 3. As illustrated in FIG. 3, the hypergeometric probability method in this example greatly underestimates ($m^{0.05}$=42)

the significance of the overlap set in comparison with the overlap probability method ($m^{0.05}=19$) for the SJIA and ERA overlap.

Example 4: SJIA and RA Overlap Probability Comparison of a Simulation and Formula II Data from the SJIA/RA study, X=30,887; Y=3,690; M=3,489; x=805; and y=329 (see Table 2, line 1) were also subject to a simulation so that simulated probability values for overlaps (m's) of selected sizes performed by a simulation as described elsewhere herein could be compared with the overlap probability as calculated using Formula II. The simulation for m values from 0 to 329, are shown in Table 3.

TABLE 3

Overlap Probabilities between SJIA and RA Gene List: Comparison of Formula II and a Simulation

| m | p (Formula II) | p (Simulation) |
|---|---|---|
| 0 | 2.608299E−04 | 2.632700E−04 |
| 1 | 2.190940E−03 | 2.186550E−03 |
| 2 | 9.162027E−03 | 9.181410E−03 |
| 3 | 2.543165E−02 | 2.541989E−02 |
| 4 | 5.271416E−02 | 5.267343E−02 |
| 5 | 8.703094E−02 | 8.701108E−02 |
| 6 | 1.192169E−01 | 1.191774E−01 |
| 7 | 1.393635E−01 | 1.394046E−01 |
| 8 | 1.419246E−01 | 1.419545E−01 |
| 9 | 1.279082E−01 | 1.279012E−01 |
| 10 | 1.032906E−01 | 1.032740E−01 |
| 11 | 7.549274E−02 | 7.547997E−02 |
| 12 | 5.035360E−02 | 5.038358E−02 |
| 13 | 3.086444E−02 | 3.086540E−02 |
| 14 | 1.748885E−02 | 1.751286E−02 |
| 15 | 9.207787E−03 | 9.217760E−03 |
| 16 | 4.524495E−03 | 4.508110E−03 |
| 17 | 2.083053E−03 | 2.088820E−03 |
| 18 | 9.016672E−04 | 9.050100E−04 |
| 19 | 3.680825E−04 | 3.677800E−04 |
| 20 | 1.421008E−04 | 1.421300E−04 |
| 21 | 5.200944E−05 | 5.323000E−05 |
| 22 | 1.808768E−05 | 1.856000E−05 |
| 23 | 5.989513E−06 | 6.470000E−06 |
| 24 | 1.892015E−06 | 1.980000E−06 |
| 25 | 5.711251E−07 | 6.400000E−07 |
| 26 | 1.650067E−07 | 2.000000E−07 |
| 27 | 4.569548E−08 | 6.000000E−08 |
| 28 | 1.214610E−08 | 0.000000E+00 |
| 29 | 3.102709E−09 | 0.000000E+00 |
| 30 | 7.626009E−10 | 0.000000E+00 |
| . . . 329 | 0.000000E+00 | 0.000000E+00 |

As shown in Table 3, the overlap probability formula as described herein provides an exceptionally accurate p-value as compared with a simulation, even at low values of m.

The present invention may be embodied in other specific embodiments without departing from the spirit or essence of the invention.

What is claimed is:

1. A method for predicting whether a patient will benefit from treatment with a therapeutic agent, comprising:
receiving a first dataset comprising a number of gene sequences (X) obtained from a first patient having a disease and a second dataset comprising a number of gene sequences (Y) obtained from a second patient having the disease, wherein the first dataset and the second dataset are non-identical;
calculating a number of genes (M) in a gene set in common between the first dataset and the second dataset;
calculating a number of genes (x) in a first gene set of interest in the first dataset, wherein genes in the first gene set of interest associate with a positive response to the therapeutic agent;
calculating a number of genes (y) in a second gene set of interest in the second dataset, wherein genes in the second gene set of interest associate with a positive response to the therapeutic agent;
calculating a number of genes (m) in an overlap gene set representing an intersection between the first gene set of interest and the second gene set of interest;
calculating an overlap probability (p(m)) that the overlap gene set is drawn by chance by $$p(m) = \frac{C(M,m) \sum_{i=0}^{min(x-m,M-m)} [(C(M-m,i)(C(X-M,x-i-m))(C(Y-m-i,y-m))]}{(C(X,x))(C(Y,y))}$$

wherein i refers to a number of genes of interest in the first dataset that are not included in the overlap gene set but are included in both the first dataset and the second dataset,
wherein C(M,m) refers to a number of possible ways of choosing m number of genes from the gene set in common between the first dataset and the second dataset,
wherein C(X,x) and C(Y,y) refer, respectively, to a number of possibilities of choosing x number of genes of interest from the first dataset and a number of possibilities of choosing y number of genes of interest from the second dataset;
calculating a statistical significance of the overlap probability (p(m)); and
when the overlap probability (p(m)) is statistically significant, identifying genes in the corresponding overlap set as a prognostic indicator that a patient with the disease will benefit from treatment with the therapeutic agent.

2. The method of claim 1, further comprising administering the therapeutic agent to a patient for treatment of the disease.

3. The method of claim 1, wherein the first dataset comprises data received from a first microarray and the second dataset comprises data received from a second microarray.

4. The method of claim 1, wherein the first dataset and the second data set are derived independently from two overlapping populations.

5. The method of claim 1, further comprising calculating a cumulative overlap probability.

6. The method of claim 5, wherein calculating the cumulative overlap probability comprises:
calculating an overlap probability p(a) for each value of a from a=0 to a=m−1;
summing the calculated overlap probabilities from a=0 to a=m−1; and
subtracting the sum from 1.

7. The method of claim 6, further comprising calculating a critical overlap size with a specified statistical significance (S) of the cumulative overlap probability.

8. The method of claim 7, wherein calculating the critical overlap size with the specified statistical significance (S) of the cumulative overlap probability comprises:

initializing $m_{max}$ to the least of x, y, or M;

calculating a cumulative overlap probability, iterating from m=0 to the value of $m_{max}$ until a cumulative overlap probability of less than S is reached; and calculating the critical overlap size as a value of m for the calculated cumulative overlap probability that falls below S.

9. A computer readable medium storing processor-executable instructions adapted to cause one or more computing devices to:

receive a first dataset comprising a number of genes (X) and a second dataset comprising a number of genes (Y), wherein the first dataset and the second dataset are non-identical;

calculate a number of genes (M) in a gene set in common between the first dataset and the second dataset;

calculate a number of genes (x) in a first gene set of interest in the first dataset;

calculate a number of genes (y) in a second gene set of interest in the second dataset;

calculate a number of genes (m) in an overlap gene set representing an intersection between the first gene set of interest and the second gene set of interest;

calculate an overlap probability (p(m)) that the overlap gene set is drawn by chance by $$p(m) = \frac{C(M,m) \sum_{i=0}^{min(x-m,M-m)} [(C(M-m,i))(C(X-M,x-i-m))(C(Y-m-i,y-m))]}{(C(X,x))(C(Y,y))}$$

wherein i refers to a number of genes of interest in the first dataset that are not included in the overlap gene set but are included in both the first dataset and the second dataset, wherein C(M,m) refers to a number of possible ways of choosing m number of genes from the gene set in common between the first dataset and the second dataset, wherein C(X,x) and C(Y,y) refer, respectively, to a number of possibilities of choosing x number of genes of interest from the first dataset and a number of possibilities of choosing y number of genes of interest from the second dataset;

calculate a statistical significance of the overlap probability (p(m)); and when the overlap probability (p(m)) is statistically significant, assigning one or more patients having the first disease to a clinical trial for treatment with a therapeutic agent that is effective against the second disease.

10. The computer readable medium of claim 9, wherein the first dataset comprises data received from a first microarray and the second dataset comprises data received from a second microarray.

11. The computer readable medium of claim 9, wherein the first dataset and the second data set are derived independently from two overlapping populations.

12. The computer readable medium of claim 9, further comprising processor-executable instructions adapted to cause one or more computing devices to calculate a cumulative overlap probability.

13. The computer readable medium of claim 12, wherein the processor-executable instructions adapted to cause one or more computing devices to calculate the cumulative overlap probability comprise processor-executable instructions adapted to cause one or more computing devices to:

calculate an overlap probability p(a) for each value of a from a=0 to a=m−1;

sum the calculated overlap probabilities from a=0 to a=m−1; and subtract the sum from 1.

14. The computer readable medium of claim 13, further comprising processor-executable instructions adapted to cause one or more computing devices to calculate a critical overlap size with a specified statistical significance (S) of the cumulative overlap probability.

15. The computer readable medium of claim 14, wherein the processor-executable instructions adapted to cause one or more computing devices to calculate the critical overlap size with the specified statistical significance (S) of the cumulative overlap probability comprise processor-executable instructions adapted to cause one or more computing devices to:

initialize $m_{max}$ to the least of x, y, or M;

calculate a cumulative overlap probability, iterating from m=0 to the value of $m_{max}$ until a cumulative overlap probability of less than S is reached; and calculate the critical overlap size as a value of m for the calculated cumulative overlap probability that falls below S.

16. A method comprising:

receiving a first dataset comprising a number of gene sequences (X) associated with a first disease and a second dataset comprising a number of gene sequences (Y) associated with a second disease, wherein the first dataset and the second dataset are non-identical;

calculating a number of gene sequences (M) in a gene set in common between the first dataset and the second dataset;

calculating a number of gene sequences (x) in a first gene set of interest in the first dataset, wherein the first gene set of interest comprises a genetic signature of the first disease;

calculating a number of gene sequences (y) in a second gene set of interest in the second dataset, wherein the second gene set of interest comprises a genetic signature of the second disease;

calculating a number of gene sequences (m) in an overlap gene set representing an intersection between the first gene set of interest and the second gene set of interest;

calculating an overlap probability (p(m)) that the overlap gene set is drawn by chance by $$p(m) = \frac{C(M,m) \sum_{i=0}^{min(x-m,M-m)} [(C(M-m,i))(C(X-M,x-i-m))(C(Y-m-i,y-m))]}{(C(X,x))(C(Y,y))}$$

wherein i refers to a number of genes of interest in the first dataset that are not included in the overlap gene set but are included in both the first dataset and the second dataset, wherein C(M,m) refers to a number of possible ways of choosing m number of genes from the gene set in common between the first dataset and the second dataset, wherein C(X,x) and C(Y,y) refer, respectively, to a number of possibilities of choosing x number of genes of interest from the first dataset and a number of possibilities of choosing y number of genes of interest from the second dataset;

calculating a statistical significance of the overlap probability (p(m)); and when the overlap probability (p(m)) is statistically significant, assigning one or more patients having the first disease to a clinical trial for treatment with a therapeutic agent that is effective against the second disease.

17. The method of claim 16, wherein the first dataset comprises data received from a first microarray and the second dataset comprises data received from a second microarray.

18. The method of claim 16, further comprising calculating a cumulative overlap probability.

19. The method of claim 18, wherein calculating the cumulative overlap probability comprises:

calculating an overlap probability p(a) for each value of a from a=0 to a=m−1;

summing the calculated overlap probabilities from a=0 to a=m−1; and subtracting the sum from 1.

20. The method of claim 19, further comprising calculating a critical overlap size with a specified statistical significance (S) of the cumulative overlap probability.

21. The method of claim 1, wherein the first dataset and the second dataset comprise non-identical sets of genes.

22. The method of claim 1, wherein the first dataset and the second dataset comprise non-identical sets of single nucleotide polymorphisms.

* * * * *